(12) United States Patent
Jorgensen et al.

(10) Patent No.: US 6,425,414 B2
(45) Date of Patent: Jul. 30, 2002

(54) FLUID MANAGEMENT SYSTEMS

(75) Inventors: Glen Jorgensen, Marlboro; Donald Barry, Norwood; Jeremy Fennelly, Watertown; Roy E. Martin, III, Clinton; Mark Susser, Weston, all of MA (US)

(73) Assignee: ZymeQuest, Inc., Beverly, MA (US)

( * ) Notice: Subject to any disclaimer, the term of this patent is extended or adjusted under 35 U.S.C. 154(b) by 0 days.

(21) Appl. No.: 09/849,955

(22) Filed: May 4, 2001

Related U.S. Application Data

(63) Continuation of application No. 09/728,327, filed on Dec. 1, 2000, which is a continuation of application No. 09/082,201, filed on May 20, 1998, now abandoned.
(60) Provisional application No. 60/047,213, filed on May 20, 1997.

(51) Int. Cl.[7] ................................................. F17D 1/14
(52) U.S. Cl. ........................................... 137/597; 383/38
(58) Field of Search ................................ 137/255, 266, 137/91, 597, 607, 625.29; 383/38, 39, 40

(56) References Cited

FOREIGN PATENT DOCUMENTS

| EP | 682953 | * | 5/1995 |
| WO | 96/28199 | * | 9/1996 |

* cited by examiner

Primary Examiner—S. Hepperle
(74) Attorney, Agent, or Firm—Mintz, Levin, Cohn, Ferris, Glovsky and Popeo, P.C.; Ivor R. Elrifi, Esq.; Brian P. Hopkins, Esq.

(57) ABSTRACT

A device is provided for distributing a fluids from different sources to different destinations. The device receives fluids from a plurality of different sources and distributes the fluids out of a port to a destination. The device also receives fluid from the destination and transfers the fluid to another port out to another destination.

7 Claims, 16 Drawing Sheets

FLUID MANAGEMENT SYSTEMS

RELATED APPLICATIONS

This application is a continuation of U.S. application Ser. No. 09/728,327 filed Dec. 1, 2000 which is a continuation of U.S. application Ser. No. 09/082,201 filed May 20, 1998 now abandoned. This application is related to and claims the benefit under Title 35, U.S.C. §119(e) of U.S. Provisional Application Serial No. 60/047,213, filed May 20, 1997, entitled "Cell Processing System", the entire disclosure of which is incorporated herein by reference. This application is also related to U.S. application Ser. No. 09/081,733, U.S. application Ser. No. 09/082,200, U.S. application Ser. No. 09/082,341 and U.S. Pat. No. 6,175,420 all of which were filed May 20, 1998 the disclosures of all of the foregoing applications and patents are incorporated by reference herein in their entirety and were also incorporated by reference in their entirety in both of the above-noted parent and grandparent applications, Ser. Nos. 09/728,327 and 09/082,201.

BACKGROUND OF THE INVENTION

Cell processing includes steps where cells or cell elements are treated with different process chemicals or are washed and then separated from a liquid phase. For example, when preparing frozen erythrocytes for transfusion, erythrocytes are separated from cryopreservatives and other blood components such as white cells, platelet and sub-cellular debris. The entire process must be performed under sterile conditions that minimize the risk of contamination. Furthermore, whole blood is separated into its various therapeutic components such as red blood cells, white blood cells, platelets and plasma which are later transfused. There are different cell processing systems that process biological cells in an automated or semi-automated way. These systems may use a controller connected to various sensors and valves for controlling the process and helping an operator to maximize the processing efficiency. However, these systems do not interactively adjust the process based on the amount or type of the processed cells or different processing conditions.

Hospitals require a constant blood supply for transfusion. After donors provide blood, regional blood centers are responsible for ABO typing, infectious disease testing, component manufacturing, and distribution of red blood cells to hospitals. The hospitals again, test the A, B, AB, O blood group and cross match the available blood units to the appropriate patients. Since group O blood can be transfused universally, there is a high demand for group O blood, in general, and especially in emergency situations where the delay caused by typing and matching is not acceptable. Furthermore, the processed blood has a relatively short shelf life of 42 days, after which it may not be transfused. The balancing of the inventory of red blood cells is extraordinarily complex. On a daily basis, the regional blood centers must match the demand for different blood groups with the available supply held at the blood centers, and at its hospital customer sites around the country. The individual blood units are constantly moved within the system in order to match daily variation in supply and demand. In fact, individual units are frequently moved three to four times within the system before finally being transfused. Even with the best efforts by the participants to ensure that each collected unit is ultimately transfused, 4% to 8% of all collected units outdate before transfusion and must be discarded. A processing system that would reproducibly convert A, B or AB type blood to O type blood would satisfy a crucial need in this field. The availability of O blood cells would improve red cell availability, substantially eliminate red cell outdating caused by the inability to match units with recipients within the 42 day outdate window, eliminate the need for the frequent reshipment of blood units in order to match the daily supply and demand, and eliminate the need for retesting for the blood type.

Therefore, there is a wide spread need for an automated interactive cell processing system that can adjust the processing algorithm based on the type of the processed cells or the amount of the cells. Furthermore, there is a need for an automated interactive cell processing system that can assure uniform and reproducible processing condition of the same type of cells regardless of their amount being processed or the processing location.

There is also a need for an efficient means for distributing the various process chemicals and biological cells from various sources to a central processing location.

SUMMARY OF THE INVENTION

In one embodiment, a device is provided for distributing a fluids from different sources to different destinations. The device receives fluids from a plurality of different sources and distributes the fluids out of a port to a destination. The device also receives fluid from the destination and transfers the fluid to another port out to another destination.

In one embodiment, a device is provided for distributing a plurality of fluids. The device includes a plurality of ports for receiving a plurality of fluids. The device includes a channel coupled to the plurality of ports, and a first port coupled to said channel. The first port is adapted to transfer fluid from said plurality of ports a first destination, and to receive fluid from said first destination. The device also includes a second port coupled to said channel adapted to transfer fluid received on said first port from said first destination to a second destination.

In another embodiment, a connector is provided that includes a first port to receive a first source of fluid, a second port to receive a second source of fluid, a first outlet in communication with the first port, and a second outlet in communication with the second port. The first and second outlets are adapted to be attached to first and second input ports of a device for distributing the first and second fluids to a particular destination.

In another embodiment, a device is provided for storing fluids that includes a first compartment for storing a first fluid, and a second compartment for storing a second fluid.

BRIEF DESCRIPTION OF THE DRAWINGS

FIG. 11 is a rear plan view of the front plate of the distribution manifold of FIG. 8a;

FIG. 12 is a rear plan view of the membrane of the distribution manifold of FIG. 8a;

DETAILED DESCRIPTION

Figure 1:
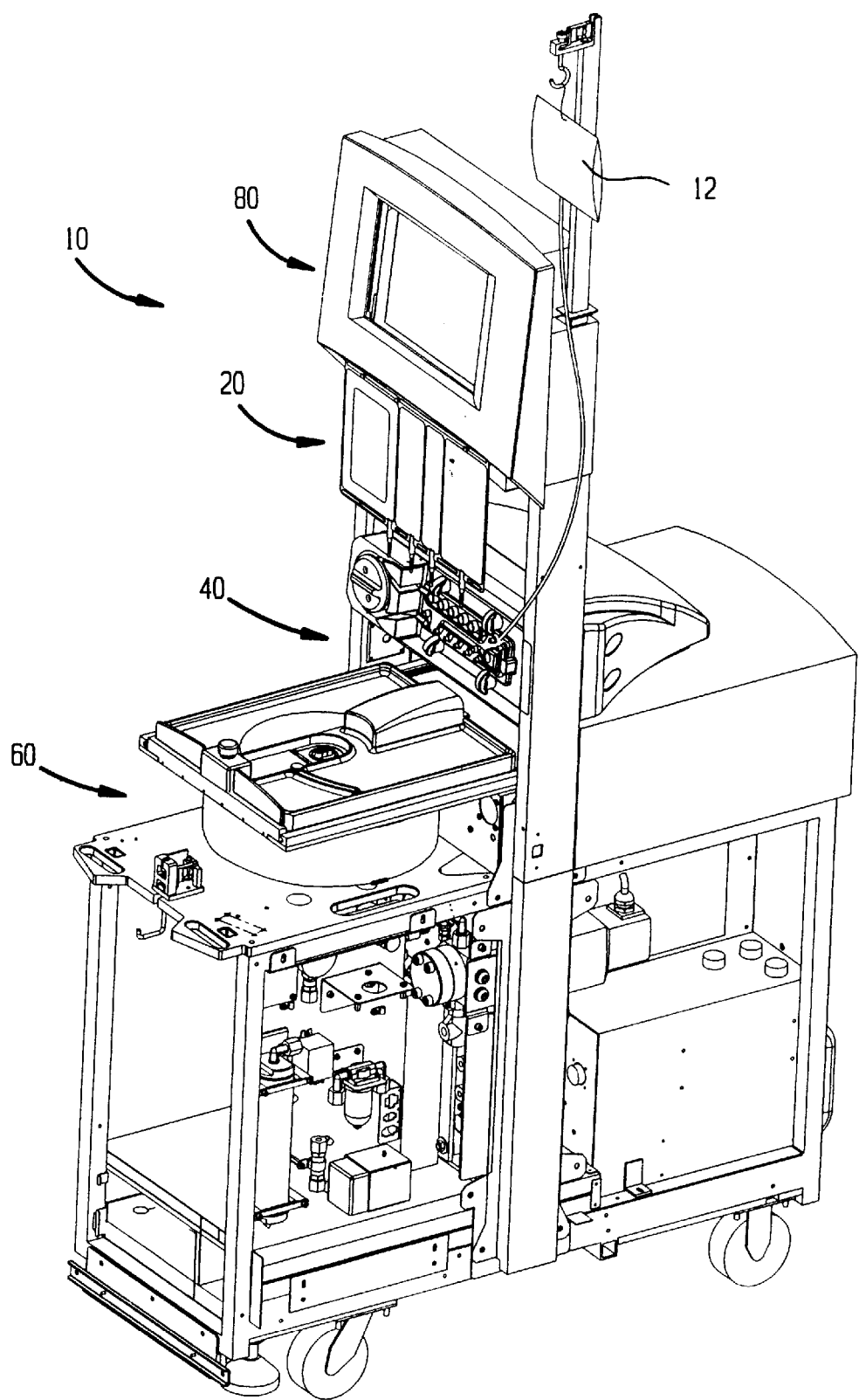
FIG. 1 is a perspective view of an interactive cell processing system.
Figure 3:
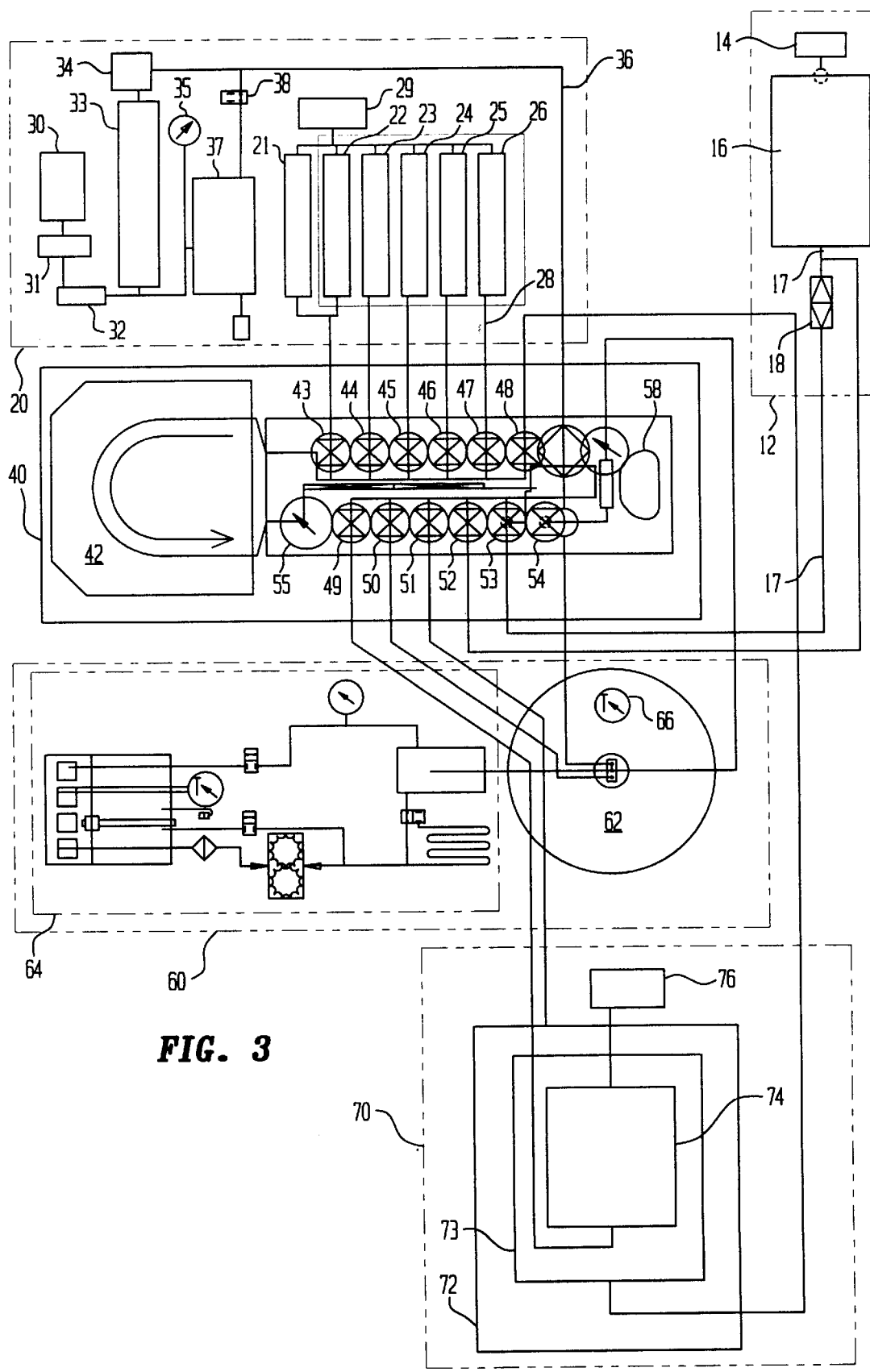
FIG. 3 is a block diagram of the interactive cell processing system of FIG. 1.

Referring to FIGS. 1 and 3, an interactive cell processing system 10 includes a cell module 12, a supply module 20, a fluid distribution module 40, a processing module 60, a collection module 70 (not shown in FIG. 1) and a control module 80. These modules are operatively interconnected for processing biological cells in a sterile environment. Cell module 12 is constructed for a short term or long term storage of biological cells for processing. Supply module 20 includes several containers for storing different process chemicals including saline, or other fluids used for washing the processed cells and also includes sterile air. The containers are connected to fluid distribution module 40 by a set of conduits. Fluid distribution module 40 includes several valves and sensors for dispensing controlled amounts of the process chemicals from supply module 20 to processing module 60 and for dispensing a known amount of the biological cells from cell module 12 to processing module 60. Furthermore, fluid distribution module 40 is constructed to direct the process waste from processing module 60 to a waste container 72 and the processed cells to a cell storage container 74, both of which are located in collection module 70, while maintaining the purity and sterility of the cells. Control module 80 directs the entire process according to a selected algorithm.

Figure 2:
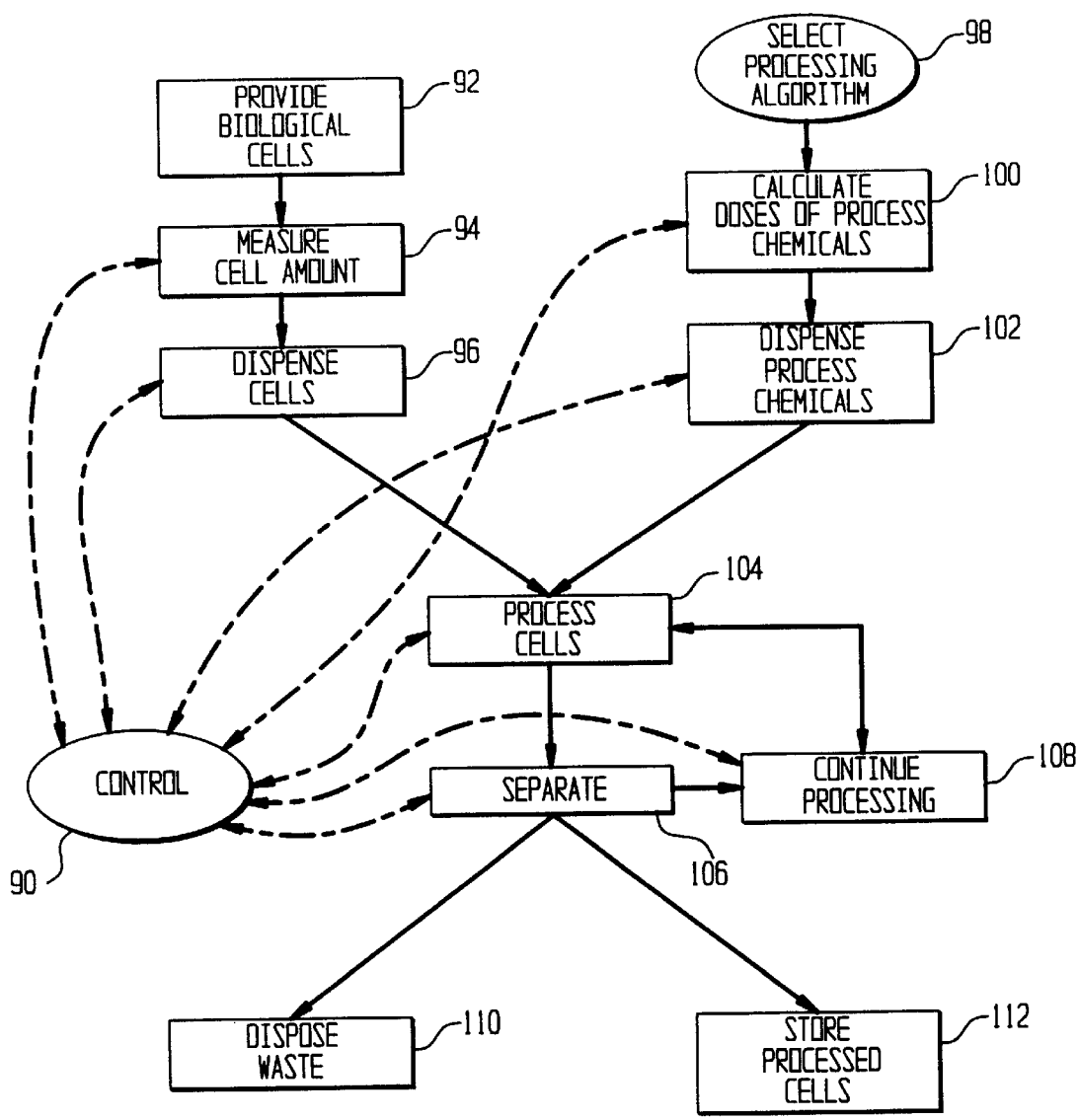
FIG. 2 is a conceptual flow diagram displaying operation of an interactive cell processing system.

In general, the operation of cell processing system 10 is shown in FIG. 2. Control module 80 executes a processing algorithm selected initially (98). Control module 80 includes a logic controller that receives real-time data from several in-line sensors arranged in a processing loop. A mass sensor (or a volume sensor) measures an initial amount of the provided biological cells (94) and sends the data to control module 80. Control module 80 controls the amount of cells dispensed to processing module 60 in accordance with the processing algorithm. Based on the provided amount of the biological cells, control module 80 also calculates the individual doses of the process chemicals (100) and directs a set of control valves to dispense the chemicals (102) in a selected order to processing module 60, again in accordance with the processing algorithm.

Control module 80 executes iteratively the processing algorithm. Control module 80 receives data from the individual sensors (e.g., a weight sensor, a volume sensor, a temperature sensor, an optical sensor, a resistance or capacitance sensor, a flow sensor, a pressure sensor or another sensor arranged to monitor the transferred matter in a liquid, gaseous or solid state). After dispensing the selected amount of one or several processing chemicals to processing module 60, control module 80 regulates the temperature and the time of processing and directs the processing module to agitate, mix or otherwise treat the cells with the process chemicals. Depending on the processing algorithm, control module 80 may manage one or several processing cycles. At the end of each cycle, processing module 60 may separate the processed cells from intermediate products and from the process waste.

During the separation process, fluid distribution module 40 detects the fluid component being expressed from processing module 60 and directs the separated components to different containers for disposal (110) or for storage (112). Each processing cycle may use a different processing chemical and different processing conditions. Cell processing system 10 can also process different types of cells at the same time or sequentially. Furthermore, cell processing system 10 may also partially process biological cells and then store them in cell storage container 74 (shown in FIG. 3), which may include a temperature control system. The processed cells may be later automatically dispensed from cell storage container 74 and processed using another processing algorithm. The processed cells may also be grown in culture prior to another use.

Based on the starting weight of the biological cells, the controller calculates the dosage of the processing chemicals. Supply module 20 includes a weight sensor 29 for providing the weight of each process chemical to the controller. During the process, the controller confirms that correct amount of each process chemical has been transferred by measuring the change in the weight of the process chemical stored in supply module 20 and the initial weight of the chemical. The process chemicals in a fluid state are pumped through a 0.2 micron filter to assure sterility. A pressure transducer is mounted up-stream from the filter. If the fluids being pumped through the filter have a variable viscosity, the controller will adjust the pumping speed to yield a constant pressure drop across the filter membrane.

Processing module 60 is designed to assure identical processing conditions (e.g., pressure, temperature, mixing, processing time or other) for large and small amounts of the biological cells provided for processing. For this purpose, processing module 60 includes a processing chamber that has a variable volume design. Depending on the volume of the processed cells and other processing chemicals transferred into the processing chamber, the controller changes the chamber volume. The volume change is achieved by a movable wall that may be a membrane. Processing module 60 includes another pressure sensor for measuring the pressure inside the processing chamber and also includes a temperature sensor for measuring the temperature inside the processing chamber. Based on the data from the temperature sensor, a heat transfer system can provide or remove heat from the processing chamber.

Cell processing system 10 may process or separate cells and/or cell elements from different liquids or solids. Such cells and cell elements include, but are not limited to, erythrocytes (i.e., red blood cells); leukocytes (i.e., white blood cells, including lymphocytes, granulocytes, and monocytes); blood cell progenitors (e.g., primitive stem cells, burst forming units, reticulocytes, megakaryocytes, etc.); cell fragments (e.g., platelets, subcellular elements such as nuclei, debris, etc.); epithelial cells; endothelial cells; mesothelial cells; cells of normal tissues (e.g., liver cells, kidney cells, bladder cells, lung cells, pancreatic cells, embryonic cells, fetal cells, etc.); cells of abnormal tissues (e.g., malignant cells), and other.

Referring again to FIG. 3, in one preferred embodiment of the cell processing system, cell module 12 includes a weight sensor 14 arranged to weigh red blood cells provided in a (plastic) bag 16. Tubing 17 connects bag 16 to a leuko filter 18 and to fluid distribution module 40. Supply module 20 includes a bag 21 with enzyme A1/B, a bag 22 with enzyme A2, a bag 23 with 140 m Molar potassium phosphate dibasic (DPP), a bag 24 with polyethylene glycol (PEG), a bag 25 with storage solution, and a bag 26 with phosphate citrate isotonic (PCI). Each bag is connected by tubing 28 to fluid distribution module 40. Weight sensor 29 is constructed to weigh any of the above-mentioned fluids located in supply module 20. Supply module 20 also includes a compressor 30 connected via a filter 31 and a check valve 32 to air reservoir 33, which stores sterile air used for cell processing. Pressure switch and sensor 34 is in communication with air tubing 36, which delivers sterile air to an air filter located in fluid distribution module 40. A regulator 37, connected to a solenoid valve 36, regulates the air pressure provided to fluid distribution module 40 and to processing module 60. Fluid distribution module 40 includes a peristaltic pump 42, and twelve valves 43, 44, . . . , and 54 connected to a set of channels for distributing the process chemicals and the cells during the automated process. The logic controller can close or open any combination of the twelve valves to redirect the fluid flowing inside the channels. A pressure sensor 55 measures the fluid pressure during the process, and an optical detector 58 monitors the fluid to and from processing module 60.

Processing module 60 includes a centrifuge 62 and an expresser system 64. An IR temperature sensor 68 monitors the temperature of the process chemicals or the cells located inside centrifuge 62. Collection module 70 includes a waste bag 72, a saline solution bag 74, and a product bag 76. Collection module 70 also includes a weight sensor 76 connected to product bag 76 and arranged to weigh the processed red blood cells.

The controller controls the volume of the processing chamber of centrifuge 62 to assure identical processing conditions for large or small amounts of the red blood cells. The processing chamber includes a flexible wall for containing expresser fluid. For small volumes, expressor system 64 pumps expressor fluid into the chamber until the pressure transducer at the chamber signals a full condition. This pre-filling step assures that different amounts of red blood cells are subjected to the same accumulated centrifugal force and mechanical stresses due to packing. Otherwise, smaller amounts would spin longer and pack harder as the expresser fluid fills the processing chamber during the expression step.

During the process, the controller receives input from IR temperature sensor 66, which measures the temperature of the RBCs. If the temperature is less than the set point, expressor of system 64 increases the temperature of the expressor fluid. Conversely, if the temperature is greater than the set point, expressor of system 64 decreases the temperature of the expresser fluid. A control loop continuously monitors the temperature of the processed cells.

Processing module 60 also includes a second pressure transducer that monitors the pressure of the sterile air on the rotating seal. If the seal is working, this pressure only fluctuates slightly between established limits. If the pressure drops below the established threshold, a warning condition is initiated that calls for a check of the rotating seal as well as other possible causes of failure.

Expressor fluid system 64 included a third pressure transducer that measures the pressure of the expressor fluid which is an indirect measure of the pressure on the red blood cells. The controller adjusts the expressor pump speed to assure that pressure is within accepted limits and cells are protected from damage. If the pressure is too low, the pump rate is increased to speed up the expression cycle. If the pressure is too high, the pump is slowed down to protect the cells from excessive pressure. This also protects the seal from excessive pressure as well.

Optical sensor 58 sensor monitors the color and the turbidity of the transferred fluids. Specifically; optical sensor 58 also monitors the supernatant expressed from the centrifuge chamber. When red cells are detected in the supernatant, the controller responds by stopping the expressor pump to avoid losing any cells to waste or responds by switching valves to collect the cells in a separate storage bag depending on which cycle is being performed.

Figure 4:
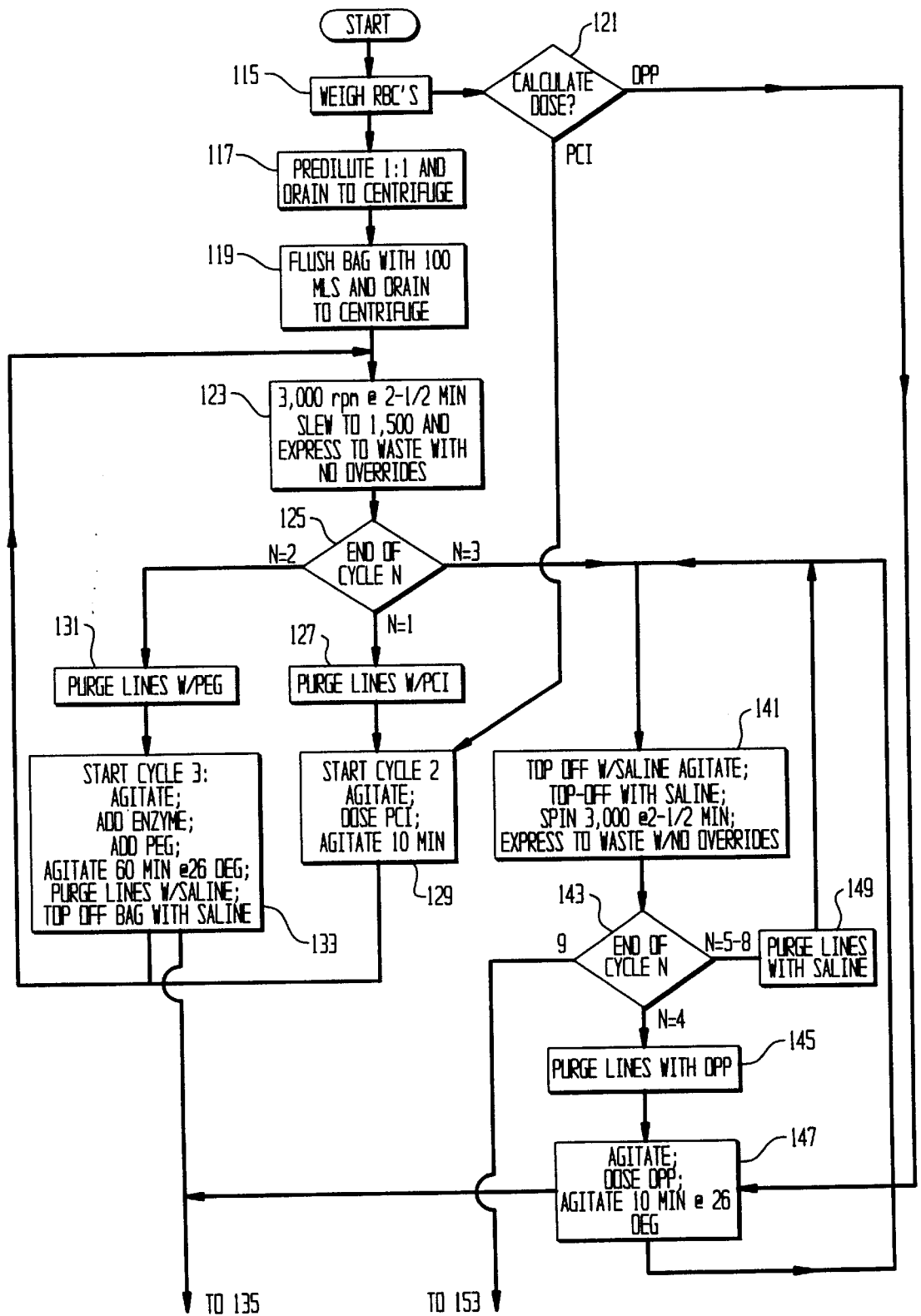
FIGS. 4 and 4A show a flow diagram of a process for enzymatic conversion of red blood cells.
Figure 4A:
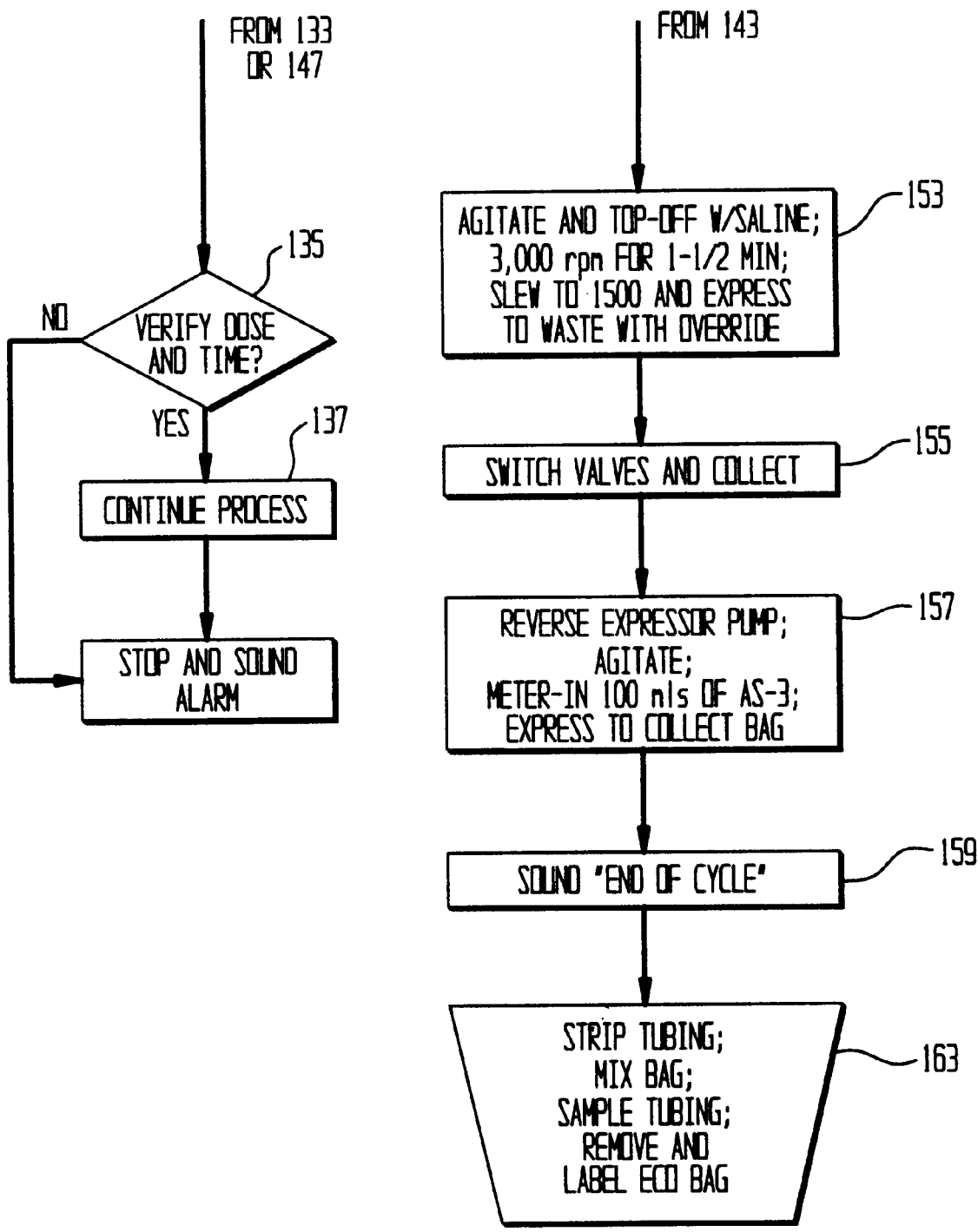

Referring to FIGS. 4 and 4A, in the preferred embodiment, the cell processing system of FIG. 3 is used for enzymatic conversion of red blood cells to type O red blood cells. The enzymatic conversion process starts in step 115 by weighting the provided amount of red blood cells. In step 117, based on the starting weight of the provided red blood cells, the system dilutes the red blood cells dispensed to the processing bag located inside centrifuge 62, shown in FIG. 3, with saline in the 1:1 ratio, and also flushes the bag with 100 ml of saline (step 119). In step 121, the controller calculates the correct dosage of PCI to obtain the ratio of 65 ml of PCI for 100 ml of red blood cells. The controller also calculates the correct dosage of DPP to obtain the ratio of 110 ml of DPP for 100 mls of red blood cells. Prior to executing step 123, the controller confirms that the correct amount of saline was transferred to centrifuge 62. In step 123, the centrifuge spins at 3000 RPM for about 2.5 minutes and then slows down to about 1500 RPM and expresses the saline waste while the washed red blood cells are left in the processing bag.

Next, in step 127, the system purges the tubing with PCI and dispenses the dose calculated in step 121, of PCI to the processing bag. PCI (Phosphate Citrate Isotonic) includes citric acid monohydrate 10.7 g/L, sodium phosphate dibasic (anhydrous) 2.7 g/L, sodium chloride 6.4 g/L suspended in one liter of sterile water having pH=2.8+0.05. The required dose is 65 mls of 2.8 pH PCI Buffer for every 100 mls of the 85 crit cell mass. In step 129, the centrifuge thoroughly mixes the solution during addition of PCI and them occasionally agitates the red blood cells and PCI mixture for about 10 minutes for equilibration to reduce the pH of the packed red blood cells from approx 7.0 to 5.5. Then, in step 123, the centrifuge expresses the separated waste (also called supernatant) while the red blood cells are left in the processing bag.

In step 131, the system purges the tubing with PEG and dispenses the calculated dose to the processing bag. In step 133, the system also adds enzymes to the processing bag, based on the amount of red blood cells measured in step 115. The enzyme includes 12.5 ml of rB-zyme or 25 ml of a suspension of exo- and endo-rA-zyme and the PEG dose is 23 ml per 250 ml of 85 crit cell suspension. The centrifuge agitates for 60 minutes at the incubation temperature of 26° C. for rB-zyme and at 37° C. for rA-zymes. The enzyme is suspended in 5.5 pH PCI Buffer, PEG is 1450 MW suspended in 5.5 pH PCI. The system also verifies the dose, the time and the temperature according to the algorithm (step 135) and continues the red blood cells conversion if all parameters are satisfied. Then, the system purges the tubing with saline and fills up the processing bag with saline. In step 123, the centrifuge spins the solution at 3000 RPM for about 2.5 minutes and then slows down to about 1500 RPM and expresses the supernatant waste while the washed red blood cells are left in the processing bag.

After the red blood cell conversion, the centrifuge expresses the supernatant (step 123). Next, in step 141, the system dispenses saline to the processing bag, agitates the mixture and spins the mixture at about 3000 RPM for about 2.5 minutes. The centrifuge expresses the waste, and the system restores the 85 crit cell mass. In step 145, purges the tubing with DPP to restore subsequently pH of converted red blood cells. In step 147, the system dispenses DPP by metering 110 ml of DPP Buffer for every 100 ml of the 85 cri cell suspension. The system dispenses 140 mM potassium phosphate dibasic with pH 9.0±0.1 (DPP) that includes potassium phosphate dibasic (anhydrous) 24.4 g/L suspended in one liter of sterile water. The centrifuge mixes thoroughly the liquid during addition of the buffer and equilibriates at 26° C. for 10 minutes also mixing occasionally during the equilibration. Next, in step 141, the system fills the processing bag with saline, agitates the mixture, and expresses the waste while the red blood cells are left in the processing bag.

Next, this system purges the lines with saline and washes the red blood cells several times by filling the processing bag with saline and subsequently expressing the waste (steps 141, 143 and 149). These steps remove the residual buffer, enzyme, PEG and phosphate to a level approximately equivalent to 99.9999%. After expressing the used saline in the last washing cycle (step 153), the system restores the 85 crit cell mass.

The controller directs fluid distribution module 40 to switch the tubing to collect the processed red blood cells in storage bag 74. This process is controlled by optical detector 58 (shown in FIG. 3). After the optical detector detects red blood cells, in step 155, the expresser pump reverses its pumping cycle to draw back into the processing bag the red blood cells from the tubing located between the processing bag and the optical detector. This is done to minimize the loss of red blood cells. Then, fluid distribution system 40 redirects the expressed red blood cells to storage bag 74. When the processing cycle is completed (step 157) the controller meters 100 mls of nutracell storage solution for 250 ml of the 85 crit cell suspension. This solution is then stored in the storage bag made from a material approved for 42-day storage (step 163).

This embodiment of the cell processing system is used for enzymatically converting blood type as described, for example, in U.S. Pat. Nos. 4,330,619, 4,427,777 and 4,609,627 by Goldstein.

Figure 5:
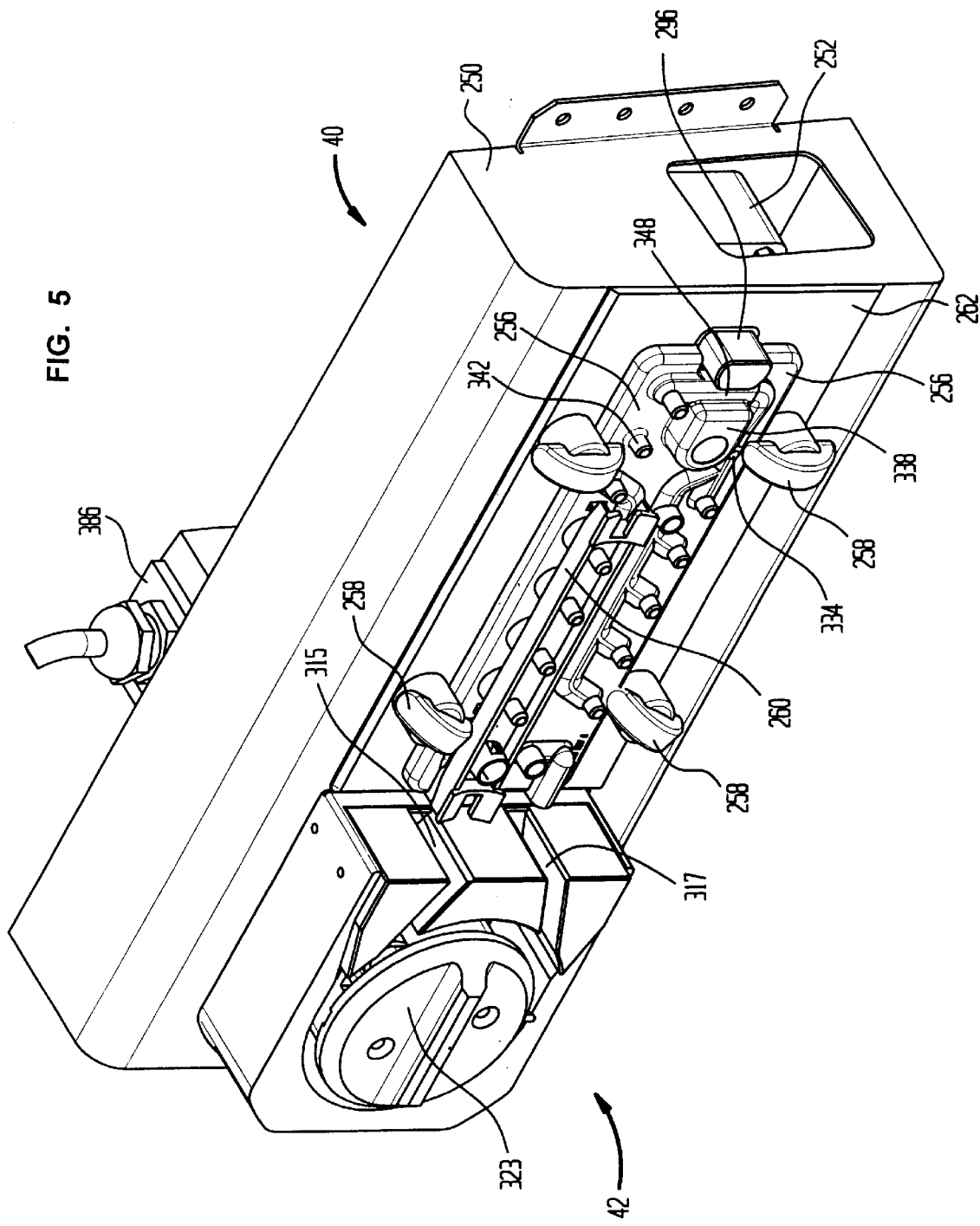
FIG. 5 is a perspective view of a fluid distribution module.
Figure 6:
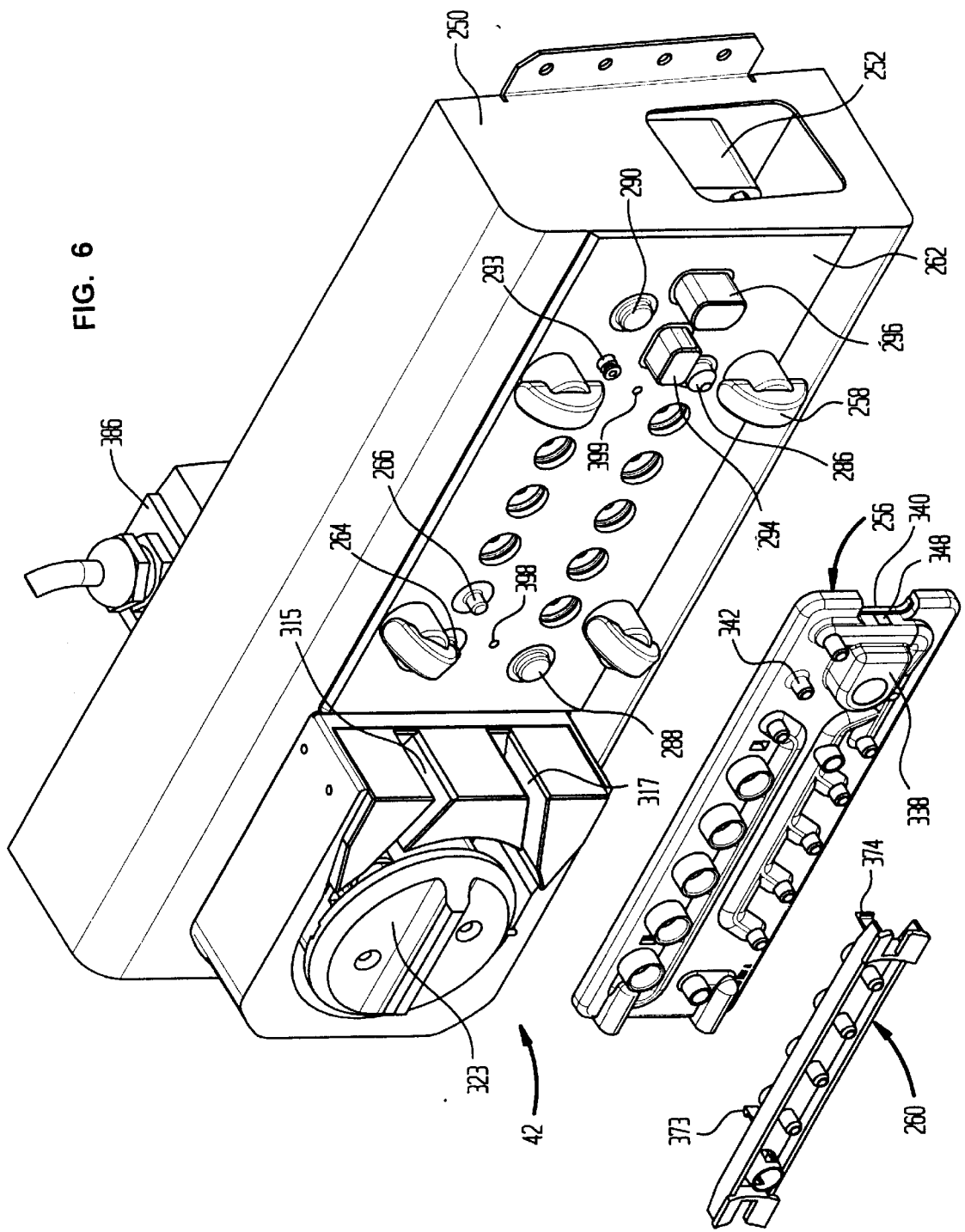
FIG. 6 is a partially exploded view of the fluid distribution module of FIG. 5.
Figure 7:
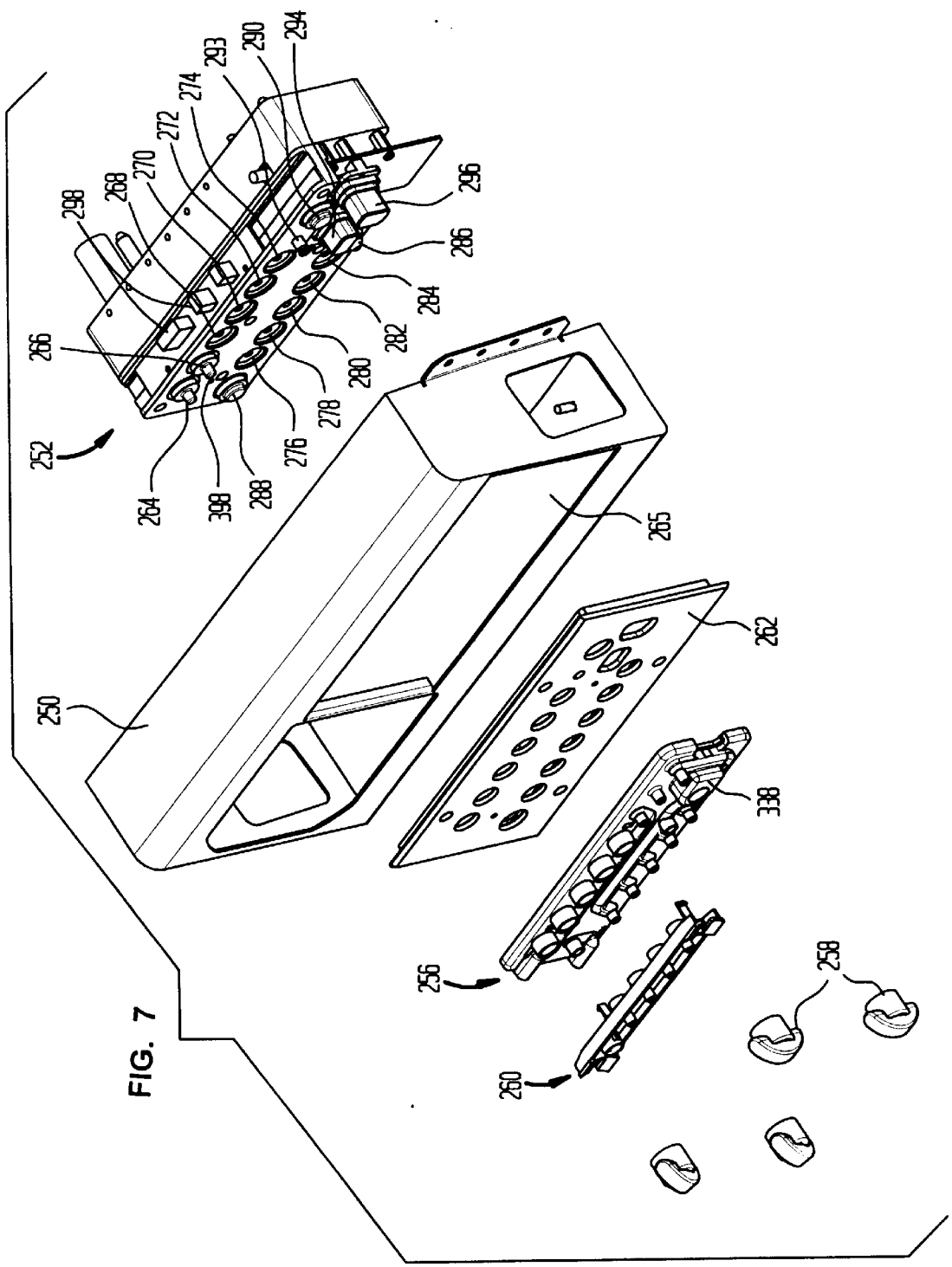
FIG. 7 is a further exploded view of the fluid distribution module of FIG. 6, showing a pump valve assembly, housing, fluid distribution manifold, connector, and spring knobs of FIG. 6.

Fluid distribution module 40 is shown in FIGS. 5–7. The fluid distribution module is part of a fluid management system that coordinates the delivery fluids including: biological cells, process chemicals, solutions, fluids, reagents, etc. to conform with a processing algorithm executed by control module 80. Generally, the fluid distribution module controls the delivery of fluids from supply module 20 and cell module 12 to the processing module 60 (see FIGS. 1 and 3), as well as the expression of fluids from the processing module 60. The fluid distribution module is a device comprised of pumps, valves, pressure management devices, and other components useful in the management of a multiplicity of different fluids from different sources.

Referring to FIGS. 5–7, the main components of the fluid distribution module are a housing 250, a pump valve assembly 252 mounted in the housing, and a distribution manifold 256 mounted on the housing on platen 262. The housing 252 can be formed from sheet metal. Also mounted on the housing 250 is peristaltic ("roller") pump 42. A connector 260 is attachable to the distribution manifold and receives tubing (see FIG. 14) from different sources of fluids to be transferred to the manifold.

The distribution manifold 256 includes a plurality of ports connected to interior runner channels for transferring fluid from one port to another. The ports are connectable to different sources or destinations of fluid.

The distribution module 40 is arranged so that the distribution manifold 256 is easily attachable to the housing 252 so that it may be a single use disposable device which can be replaced after the processing cycle is complete for a bag 16 of biological cells. The distribution manifold 256 is easily attachable and detachable to the housing through the use of spring knobs 258 (see FIG. 6). To attach the manifold, the spring knobs are rotated horizontally, the manifold is placed on platen 262, the spring knobs are pulled out, rotated vertically and released to bias the manifold against the platen.

The platen 262 is seated in a recess 265 of housing 250. The platen 262 is an intermediary between the distribution manifold 256 and the pump valve assembly 252. The pump valve assembly includes a series of solenoids which can be energized to retract normally extended plungers 264, 266, 268, 270, 272, 274, 276, 278, 280, 282, 284 and 286 and thereby open corresponding valves 43–48 and 49–54 (FIG. 3) associated with corresponding ports 302, 304, 306, 308, 310, 312, 324, 326, 328, 330, 332, 334 (FIG. 8) on the distribution manifold used to transfer fluids to and from the manifold 256. As explained in detail below, a plunger, when extended, deflects a flexible membrane within distribution manifold 256 to close a particular port so that fluid cannot enter or exit the particular port; when the solenoid associated with a plunger is energized the plunger is retracted to open the associated port, or channel, and permit fluid entry or exit.

Also supported by the pump valve assembly 252 are: load cells 288 and 290 which are used to sense the fluid pressure at two points within the distribution manifold 256; a sterile air hose and filter 293; and optical sensor 58 including an emitter 294 and a detector 296. Hall effect sensors 298 are used to detect the position of the plungers 264–286.

Platen 262 includes variously shaped holes 300 to accommodate the plungers 264–286, load cells 288 and 290, emitter 294 and detector 296 of the optical sensor, and sterile air hose 293 (see FIGS. 6 and 7). To prevent fluids from entering the pump valve assembly 252, individual silicon plunger membranes can be placed over each plunger, as well as the two load cells, and will seal the respective holes 300 of the platen 262. Thus, the plungers 264 and 266 seen in FIG. 6 are covered by such membranes. In FIG. 6, plungers 264 and 266 are shown in the normal (i.e., non-energized) position in which the ports associated with the plungers 264–266 would be shut off. When attaching the distribution manifold to the platen 262 all of the solenoids are energized so the plungers do not interfere with the placement of the manifold.

The distribution manifold 256 is comprised of three main parts: a front plate 301, a flexible membrane 303 and back plate 305. The membrane is compressed between the front and back plate to form sealed channels in the manifold. The back plate is ultrasonically welded to the front plate, however, other methods of joining plastics may be used, for example, mechanical snaps, adhesives, solvents, etc. Like the platen 262, the back plate 305 also includes holes 307 which match with the holes of the platen 300 to accommodate the various elements of the pump valve assembly 252, and expose portions of the flexible membrane 303. For example, to close the valve associated with a particular port, a solenoid plunger passes through hole 307 of the back plate 305 and deflects the flexible membrane 303 toward the front plate to shut off fluid flow in a port or a channel of the front plate 301.

Figure 8:
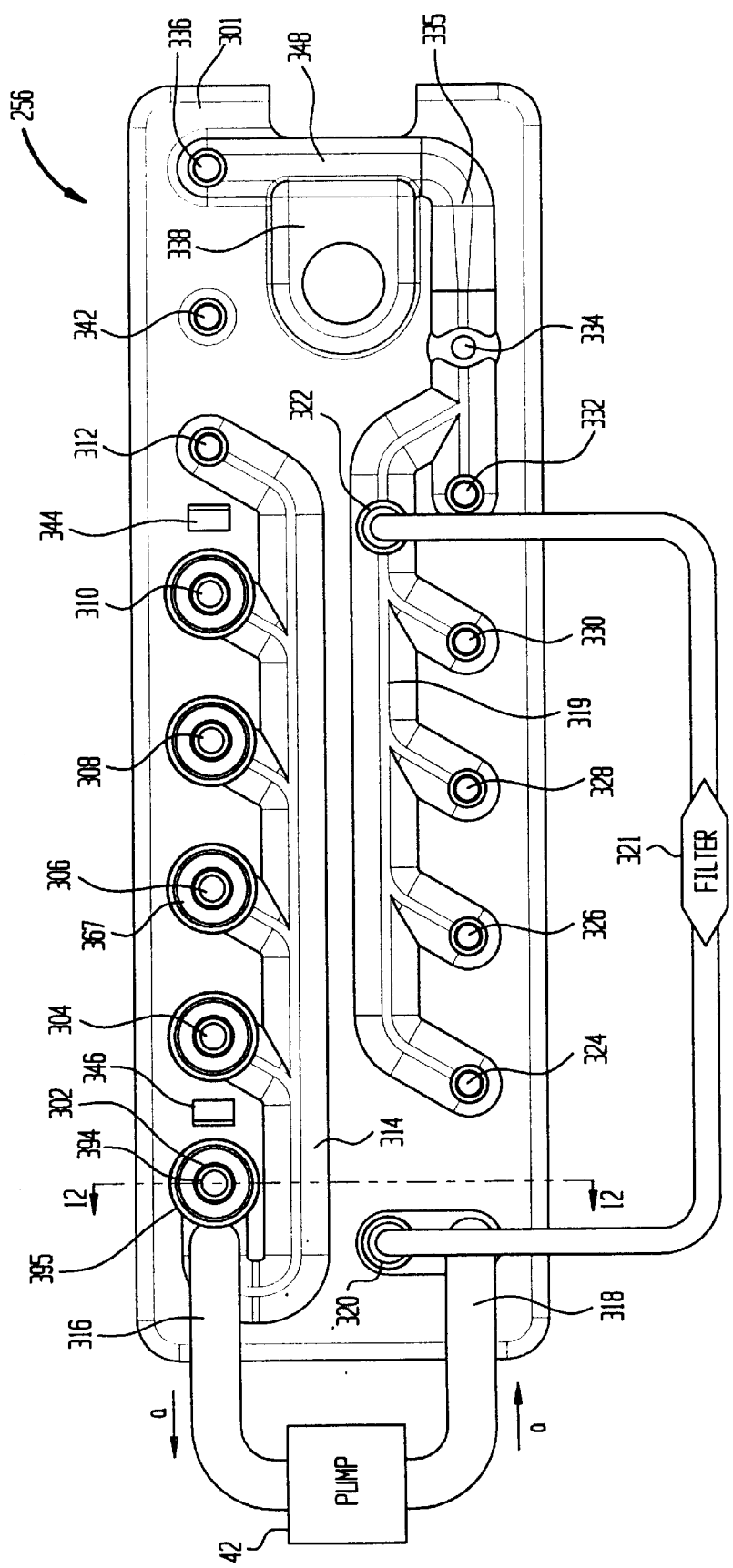
FIG. 8 is a front plan view of the distribution manifold of FIGS. 5–7, and a schematic view of a pump and filter.
Figure 9:
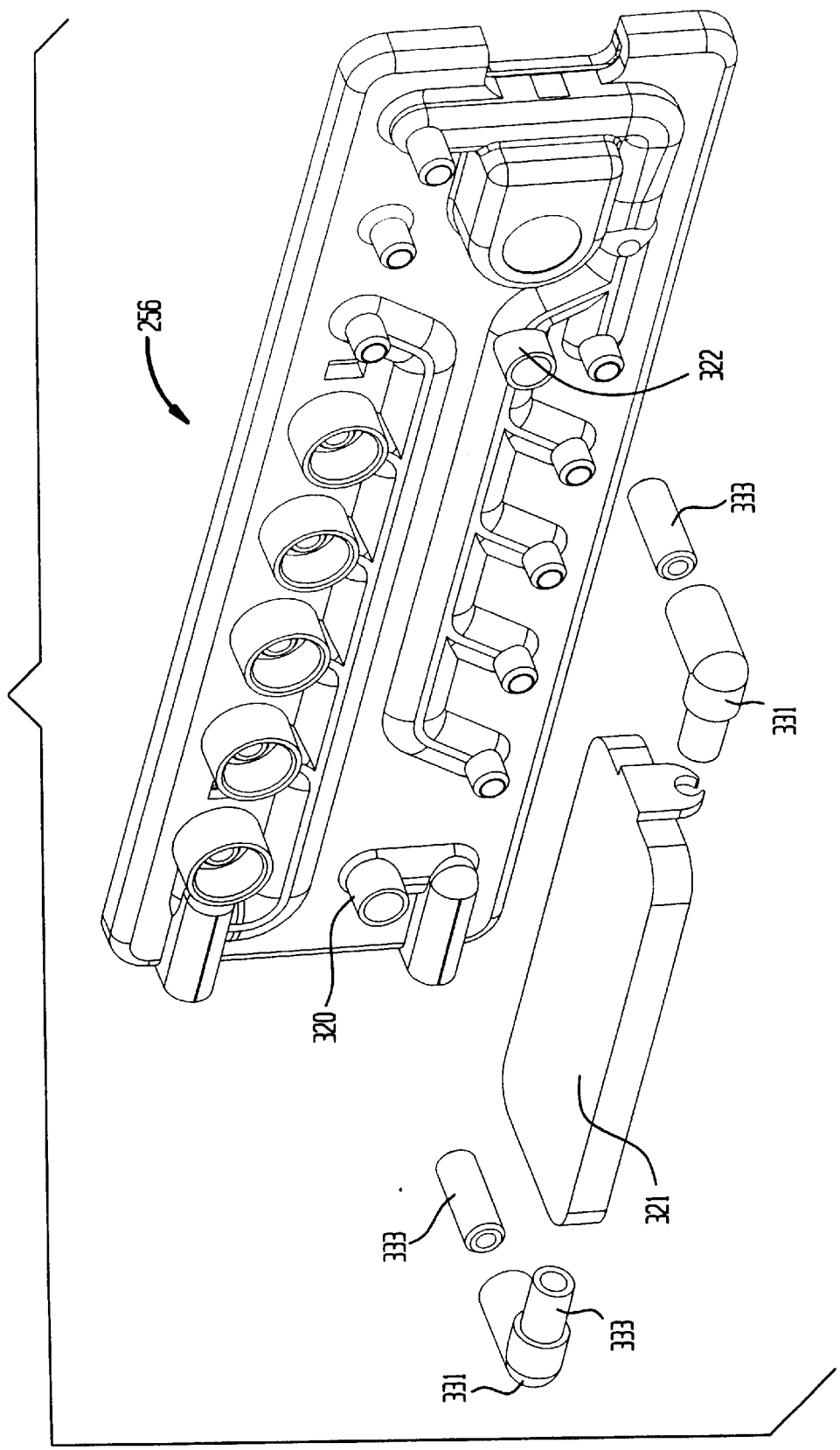
FIG. 9 is an exploded view of the distribution manifold and filter of FIG. 8.

As seen in FIG. 8, ports 302, 304, 306, 308, 310 and 312, feed to a first distribution manifold channel 314. As stated above, these port are opened and closed by plungers 264, 266, 268, 270, 272 and 274. Different process chemicals can be fed via tubing to each port 302–312. For example, as described in the preferred embodiment described with reference to FIGS. 3 and 4 above, enzymes A1/B and A2 can be attached to port 302 (from bags 21 and 22), DPP to port 304 (from bag 23), PEG to port 306 (from bag 24), storage solution to port 308 (from bag 25), PCI to port 310 (from bag 26), and saline solution to port 312 (from bag 74). Ports 302–310 are adapted to receive a connector 260 (described below) to which tubes from supply module 20 are attached.

Fluid will flow from a source connected to any of these ports into channel 314 (if the plunger for that port is retracted) and exit at outlet 316 when pump 42 is operating. Tubing connects outlet 316 to inlet 318. As shown schematically by arrows "a" in FIG. 8, the movement of fluid is from manifold channel 314. Fluid is transferred from 316 to 318 by a peristaltic pump (see FIG. 5) through which the tubing passes that connects outlet 316 to inlet 318. The pump has inlets 315 and 317 which receive the tubing, and a rotating roller 323 that rotates counterclockwise and continually pinches the tube along its length to generate a vacuum effect, sucking fluid from outlet 316 to inlet 318. Motor 386 causes roller 323 to rotate.

The fluid will proceed to port 320 and exit the manifold via tubing which is connected to a filter 321. The filter is a bacteriostatic filter having, for example, a 0.2 micron pore size manufactured by Pall Inc., and filters out contaminants which may be in the fluid. Two filters can be used in parallel to increase the rate of fluid flow which is slowed by the filter. The output of the filter 321 is coupled via tubing to another port 322 where the fluid enters a second manifold channel 319 of the manifold. Ports 320 and 322 do not have solenoid plungers associated therewith and thus are not valved ports. The filter is connected to ports 320 and 322 using elbow connecters 331 and small pieces of plastic tubing 333.

Ports 324, 326, 328, 330, 332 and 334 are also connected to manifold channel 319. Flow to these ports is controlled by solenoid plungers 276–286, respectively, corresponding to valves 49–54 (FIG. 3). These ports (and port 312) are adapted to be connected directly to tubing, unlike ports 302–310 which are adapted to receive connector 260 for reasons stated below. Ports 324–332 are two-way ports in that fluid can enter or exit from these ports. In the processing methodology described above with reference to FIG. 3, the ports are connected as follows: port 324 is connected to product bag 76, port 326 is connected to the processing module to provide a rinse saline solution, port 328 is coupled to the waste bag 72, port 330 is coupled to cell bag 16 (bypassing leukocyte filter 18), and port 332 is coupled to cell module 12 to receive unprocessed biological cells.

Using the distribution manifold 256, any fluid received on ports 302–312 can be distributed out any of ports 324, 326, 328, 330, 332 and 336. To distribute a fluid from ports 302–312 to ports 324, 326, 328, 330 or 332, gate valve 334 is closed by plunger 286 and the solenoid plunger associated with the desired port 324, 326, 328, 330 or 332 is energized and retracted to open the port so that fluid may pass. For example, saline solution received on port 312 can be pumped out of port 330 to dilute biological cells contained in cell bag 16 (bypassing leukocyte filter 18), or can be pumped out of port 326 to rinse the processing module 60. The rinse from port 326 is sent into and expressed out of the processing module and pushes the remaining cells in the line through port 336, valve 334 and out of port 324 to the product bag.

Alternatively, ports 324–332 could be kept closed, gate valve 334 opened, and fluid from any of ports 302–312 could exit out of port 336 to processing module 60. During cell processing described above, each fluid source connected to ports 302–312 is pumped into the processing module 60 at different times during the processing procedure (see FIG. 4).

A source of fluid received on one of ports 324–332 also could pass through gate valve 334 to a third manifold channel 335 and exit port 336 to processing module 60. For example, biological cells received from cell bag 16 connected to port 332 will travel through the manifold 335 and out of port 336 to the processing module 60. As with fluids received via any of ports 324–332, the cells travel from the bag, 16 through the manifold 256 and to the processing module 60 via gravity, since the cell bag is placed above the distribution manifold and the distribution manifold is above the processing module 60.

Fluids can also be expressed off from the centrifuge 62 of the processing module 60, traveling into port 336, through channel 335 and gate valve 334, to any of ports 324–332. For example, in the preferred embodiment described above the centrifuge 62 will express off waste and product to ports 328 and 324, respectively.

Third manifold channel 335 includes a cuvette 348 that leads to port 336 which is connected via tubing directly to processing module 60. The cuvette 348 is where processed fluid from processing module is detected by the optical sensor 58. The emitter of the optical detector is 294 is received in a cover 338 of the front plate 301 on one side of the cuvette, while the detector 296 is disposed in recess 340 on an opposing side of the cuvette. Thus, the detector can detect infrared light emitted through the fluid within the cuvette and detect the change to red blood cells that occurs after waste is expressed off by the centrifuge of the processing module 60. When the change is detected port 328 connected to the waste bag 72 is closed, and the process can either send the red blood cells back to the processing module 60 for further processing, or, if the process is finished, send them to the product bag by opening port 324.

The load cell 288 of the pump valve assembly 252 (see FIG. 6) is disposed beneath inlet 318 and port 320 to sense the fluid pressure being received in inlet 318. Load cell 288 senses high-pressure conditions which occur, for example, when the processing module is filled with fluid. For example, if fluid from one of ports 302–312 is being pumped to the processing module 60, when the processing module is filled the pressure will rise dramatically and be sensed by the load cell. The increased pressure signal is sent back to the control module which turns off pump 42. Sensor 288 also senses alarm conditions which can occur if there is a clog downstream from inlet 318 and port 320. A second load sensor 290 is placed beneath port 336 and senses the pressure in the centrifuge seal of the processing module 60. Thus, if the pressure in the seal at the centrifuge is too great, the processing can be discontinued or centrifuge speed reduced.

The remaining port 342 receives a sterile air hose 293 and filter from pump valve assembly 252 and is connected from front plate 301 via a tubing to processing module 60 which uses the sterile air to create a pressurized sterile environment. Openings 346 and 344 receive attachment fingers 373 and 374 (see FIG. 14) of connector 260. It should be noted that the particular arrangement of the ports, recesses, and manifold channels of the distribution manifold may be configured in numerous different ways to accomplish transfer of different fluids to different locations, and the invention is not limited to the particular arrangement shown in the figures.

Referring to FIGS. 9–12, the distribution manifold has three main components, a front plate 301, a flexible membrane 303 and a back plate 305. The front plate and back plate are injection molded plastic components made of amorphous clear polymer with high flexural modulus and good impact strength such as acrylic. Other materials may be used, for example, polycarbonate (PC), styrene acrylonitrile (SAN), polyester and copolyester, clear acrylonitrile butadiene styrene (ABS), polystyrene, polymethylpentene (TPX).

The flexible membrane 303 is made of a soft silicon material chosen for its ability to resist compression set and its load tensile modulus. Other materials can be used to form the membrane, such as thermoplastic elastomers (TPE). The distribution manifold 256 is assembled by sandwiching the membrane 303 between the front and back plate 301 and 305 and ultrasonic welding the front and back plate to one another. The front and back plate exert compressive force on the membrane.

Figure 10:
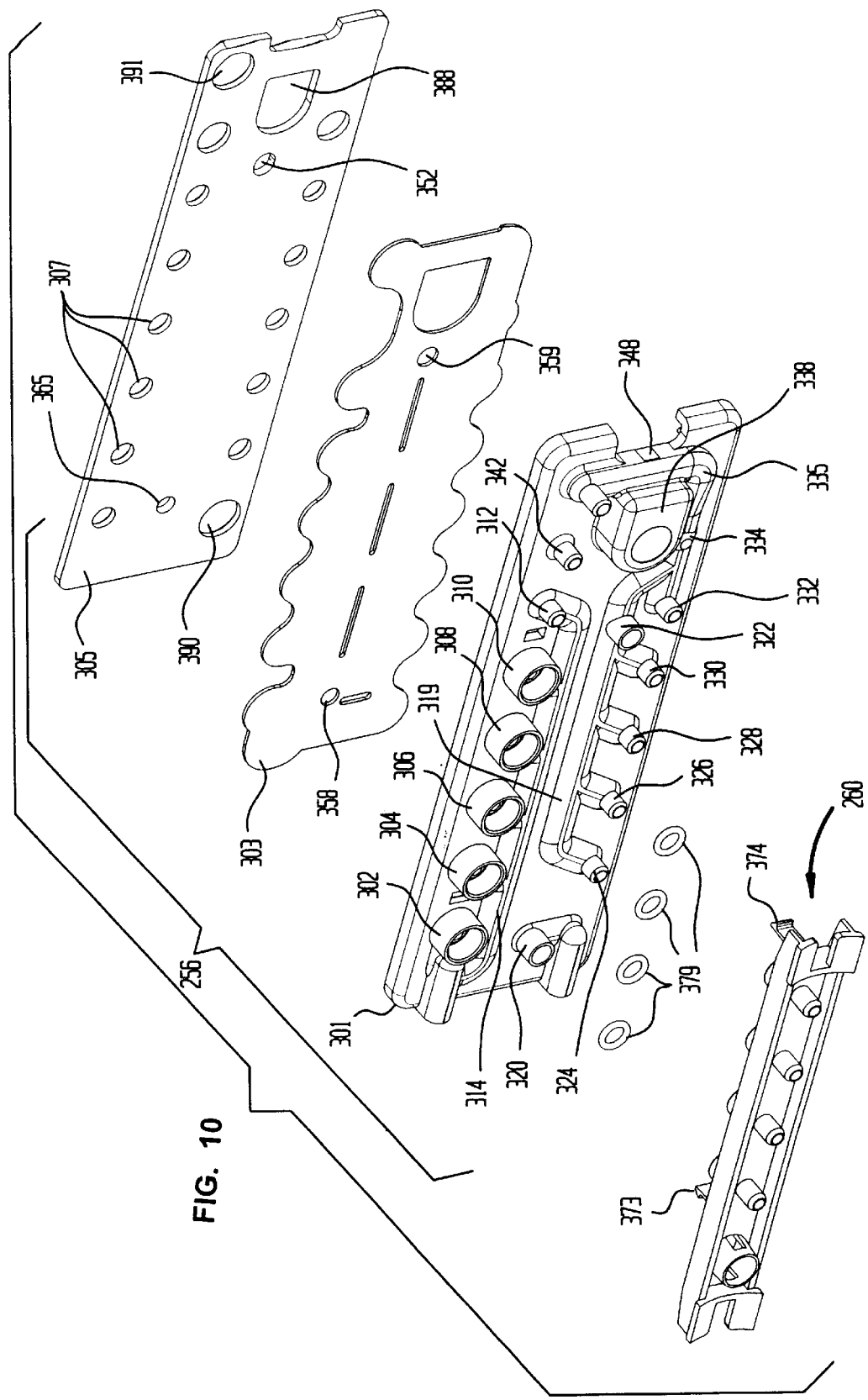
FIG. 10 is an exploded view of the distribution manifold and connector of FIGS. 5–8.
Figure 11:
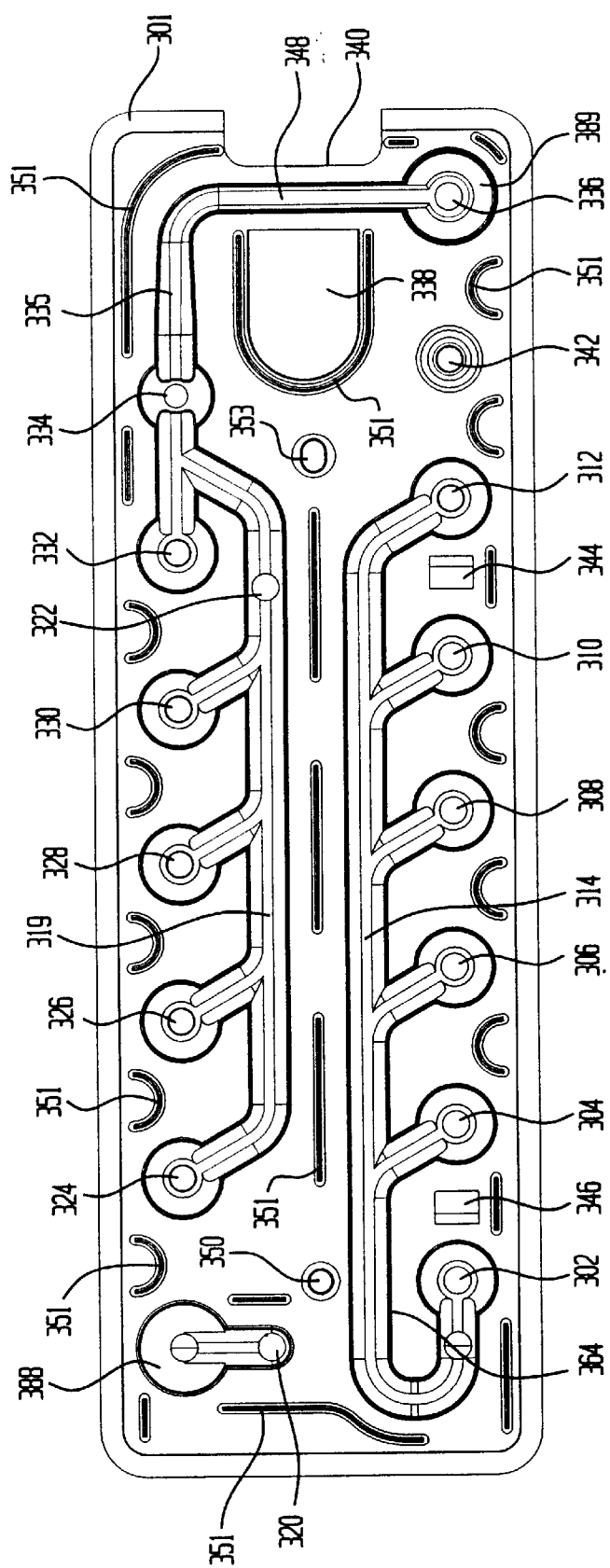

FIG. 10 shows a rear view of the front plate 301. Membrane 303 covers and seals with front plate 301 to form manifold channels 319, 314 and 335. The membrane 303 is compressed by the back plate 305 in order to form a good seal with the front plate 301 to prevent any fluid leakage out of manifold channels 314, 319 and 335, or any of the ports.

The distribution manifold 256 is constructed by laying the membrane 303 (as it is oriented in FIG. 11) over the rear of the front plate 301 (as it is oriented in FIG. 10). The side of the membrane that contacts the front plate is flat while the opposing side that contacts the back plate 305 includes bumps 355 which the solenoid plungers 264–284 are adapted to deflect to close the ports associated with and covered by the bumps 355 on the membrane. As seen by comparing FIGS. 9 and 10, bumps 355 cover ports 302–312 as well as ports 324–332. A section 360 of the membrane formed without a bump and is used to close off gate valve 334 and receives a solenoid plunger (286) which is shaped slightly different to close off the gate valve 334 that connects manifold channels 319 and 335. The back plate 305 and the membrane 303 include apertures 388 and 361 through which the optical emitter passes.

Figure 12:
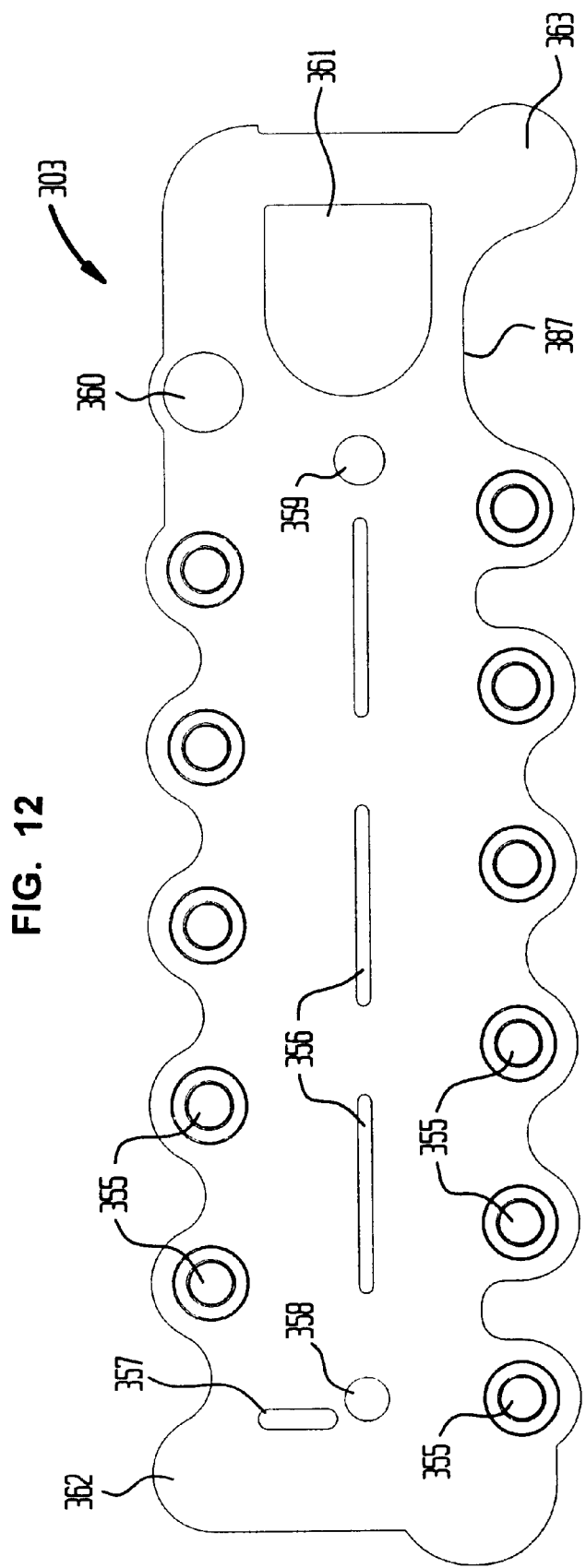

The rear surface of front plate 301 also includes a plurality of welding ribs 351 where the back plate 305 is to be ultrasonically welded to the front plate. The membrane is shaped to not interfere with the welding ribs and includes holes 356 and 357 which accommodate the ribs so they can be welded to the back plate. The weld is shown in FIG. 12 in which rib 351 is welded to back plate 305. The weld is formed at rib joint 367 in which part of the rib 351 is melted into back plate 305.

Areas 362 and 363 of the membrane 303 overlie areas 388 and 389 of the rear of the front plate. Load cells 288 and 290 contact the membrane at 362 and 363 through back plate holes 390 and 391, respectively, to sense the fluid pressure from fluid passing into inlet 318 and fluid passing into or out of port 336.

The front plate also includes pins 350 and 353 adapted to extend through the membrane 303 (through holes 358 and 359) and back plate 305 (through holes 365 and 352) in order to center the membrane 303 and back plate 305 properly on the front plate 301. The pins are hollowed (see FIGS. 10 and 12) to receive mounting pins 398 and 399 of pump valve assembly 252 which extend through the platen 262. Pins 350 and 353 are slotted to accommodate for manufacturing tolerances. The slotting of pin 353 (see FIG. 10) is oblong to accommodate the greater horizontal tolerances due to the shape of the manifold 256.

The front plate further includes openings 346 and 344 for receiving attachment fingers 373 and 374 of connector 260. To properly position and hold the membrane in place as well as to form a seal, the front plate includes raised ridges 364 (see FIG. 12) which sink into membrane 303 when it is compressed between front plate 301 and back plate 305. Solenoid plungers are received in holes 307 in the back plate and will depress and deflect the exposed membrane at bump 355 to close a respective port. The plunger closes off the port by deflecting the membrane up to seal with surface 392 (see FIG. 12) of the front plate port. The membrane is slightly thinned surrounding the button 355 at 393 in order to assist the membrane in deforming to close the port.

The cross-section shown in FIG. 12 also shows a connector port 366 attached which is part of the connector 260 (see FIG. 5) which is attached to the face of the front plate. As seen in FIG. 8, ports 302, 304, 306, 308 and 310 are shaped to accommodate connector 260 rather than directly receive tubing as ports 324, 326, 328, 330, 332 and 336 do. Alternatively, the ports 302–310 can be formed like ports 324–336 to directly receive tubing if it is not desired to use connector 260.

Figure 13:
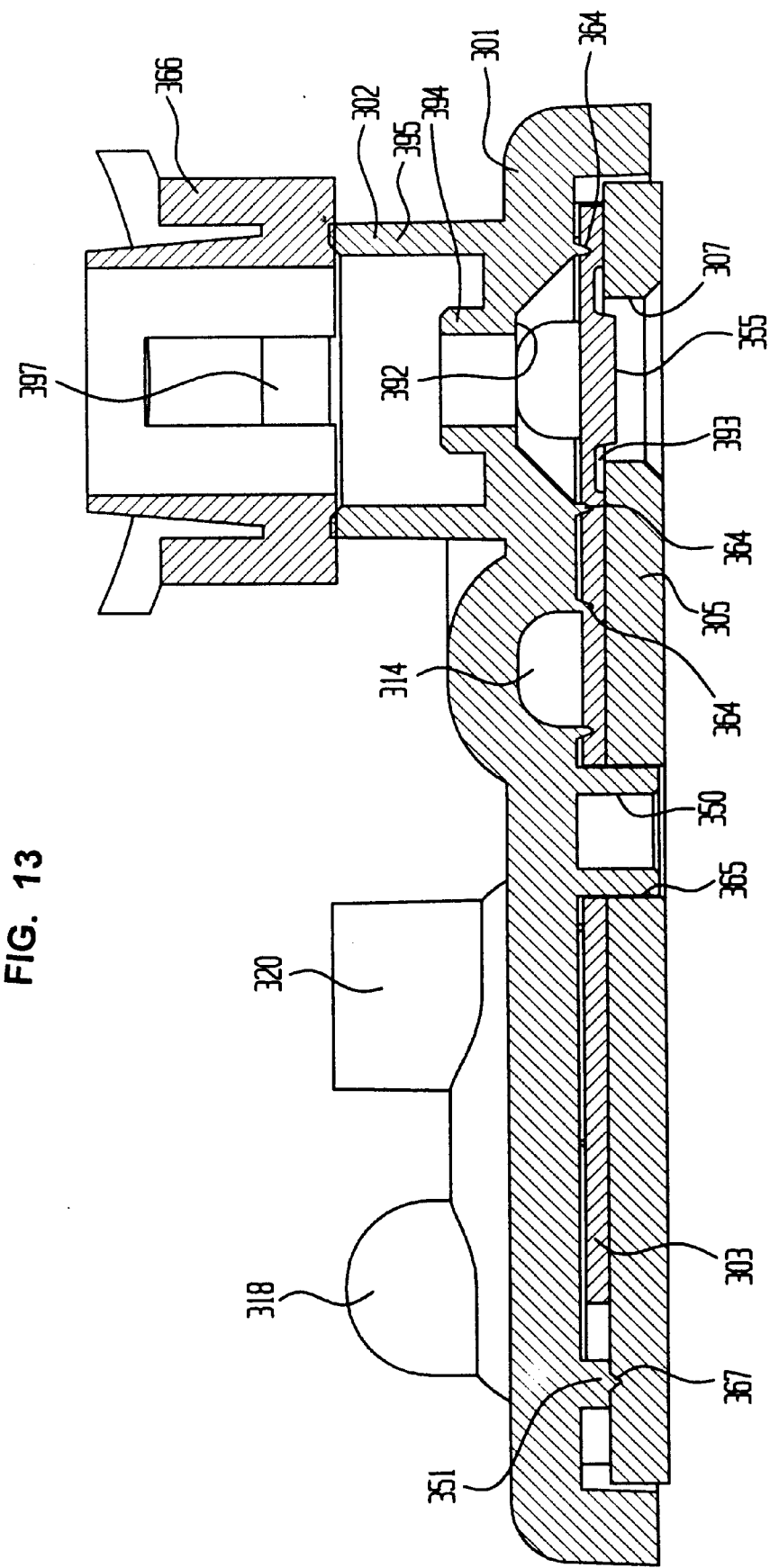
FIG. 13 is a cross-sectional view of FIG. 8, taken along lines 12—12.
Figure 14:
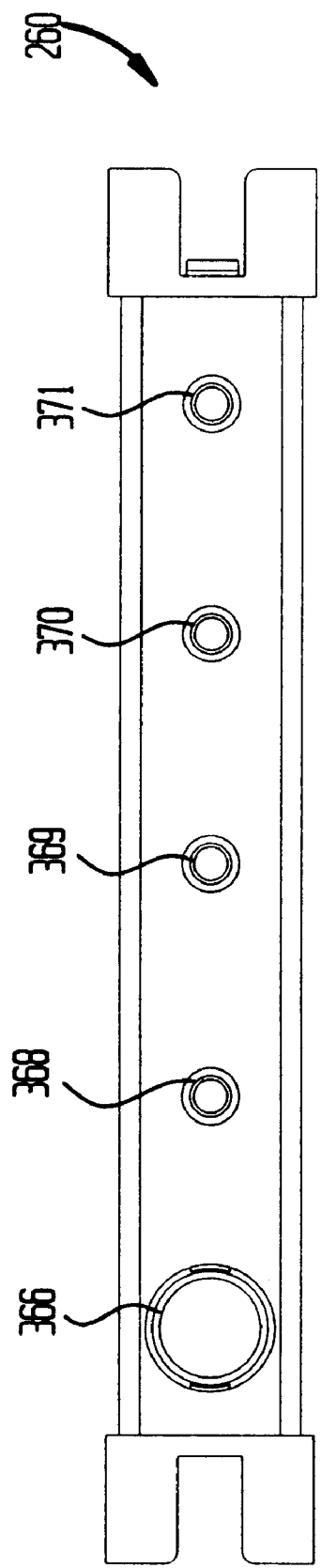
FIGS. 14 and 15 are front and top plan views, respectively, of the connector of FIGS. 5–.

As seen in FIGS. 13–14, the connector 260, which is made of injection molded plastic, includes cylindrical extensions 375–378 which are adapted to sit inside and to mate with an interior surface of ports 304, 306, 308 and 310, respectively. The connector assures that the process fluids from different sources are connected to the proper port of the distribution manifold. The cylindrical extensions are constructed to sit in between an inner ring 394 and an outer ring 395 of the port (see FIGS. 8 and 12). O-rings 379 (see FIG. 9) are adapted to sit between the extensions 375–378 and ports 304–310 to provide a seal. Attachment fingers 373 and 374 snap into the front plate openings 344 and 346.

Figure 15:
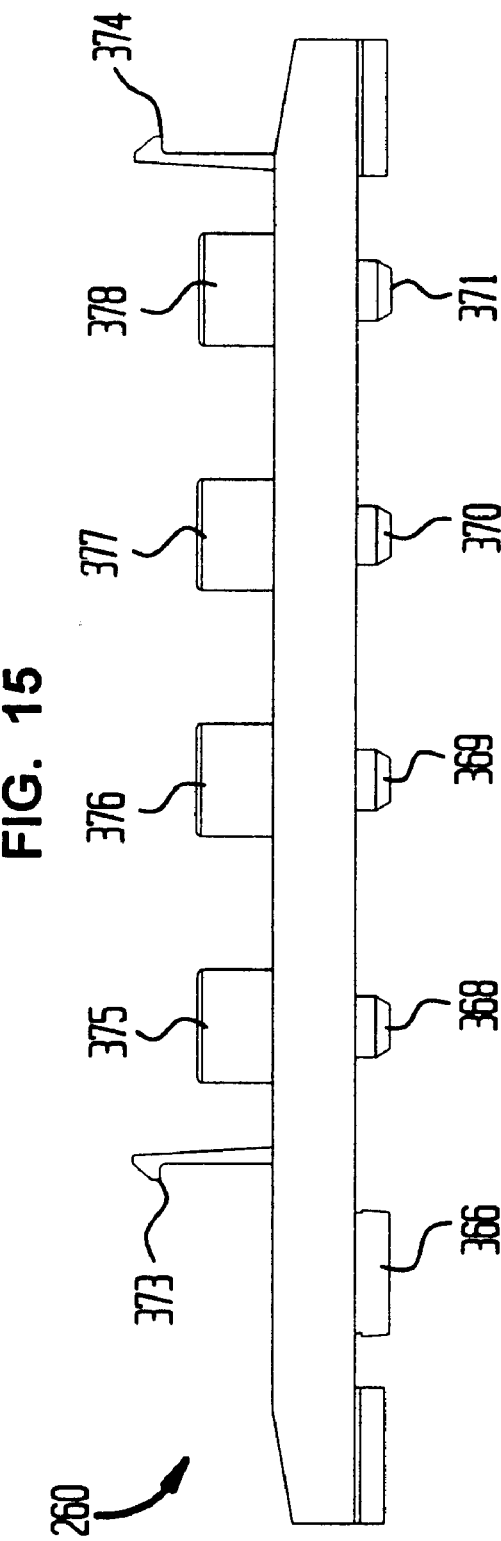
Figure 16:
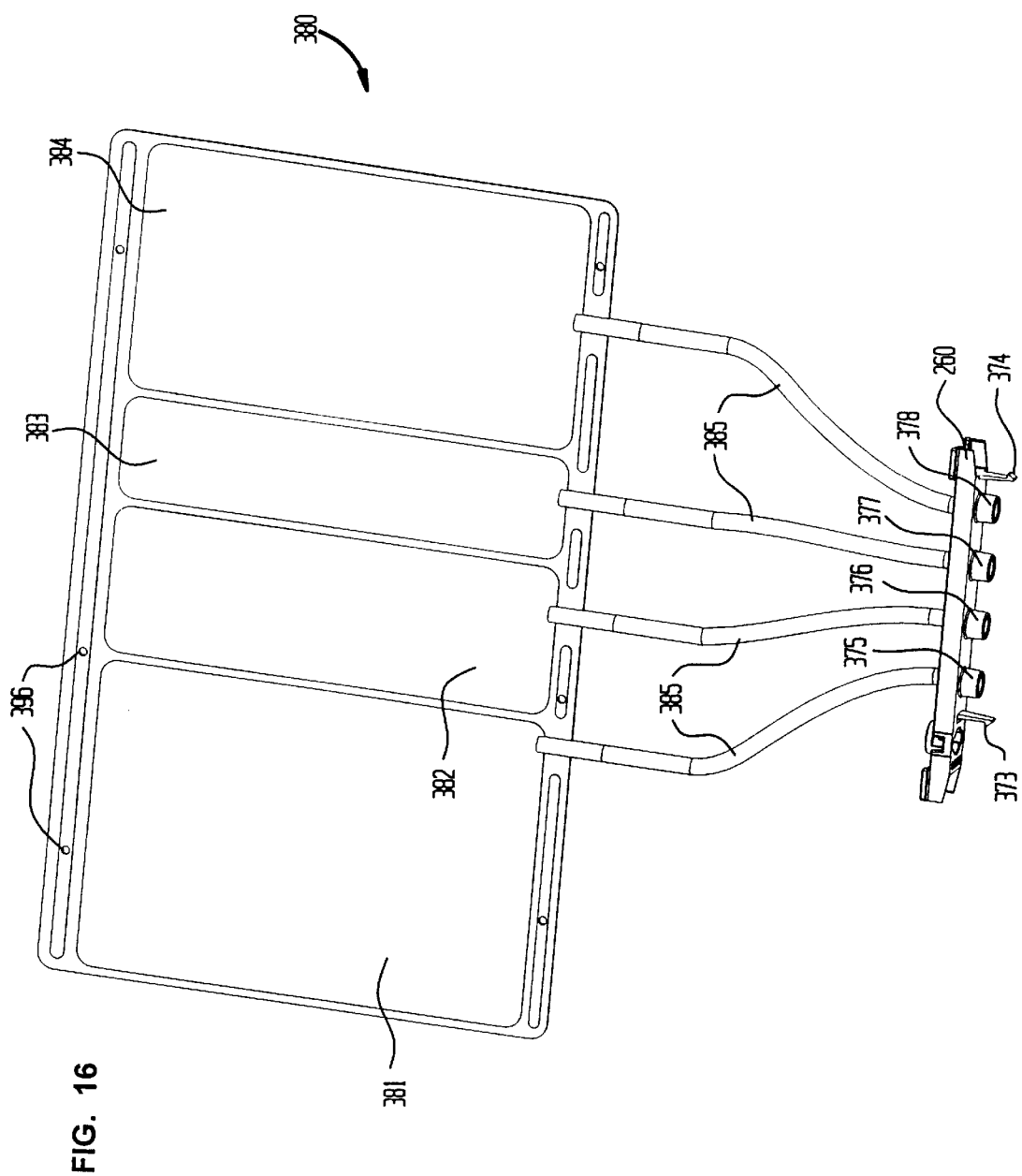
FIG. 16 is a perspective view of a multi-compartment bag connected by tubing to the connector of FIGS. 14 and 15.

Ports 368, 369, 370 and 371 of connector 260 feed to respective extensions 375–378, and are attachable to tubing which is connected to a multi-compartment bag 380 as shown in FIG. 15. The bag 380 contains compartments 381, 382, 383 and 384 which can contain different types of processing chemicals, such as DPP, PEG, storage solution (AS3), and PCI, respectively. The bag can be shipped with connector 260 attached as shown in FIG. 15. The connector 260 will assure that tubes 385 are connected in the proper order to ports 302, 304, 306, 308 and 310 of front plate 301. The bag 380 is constructed of Cryovac M312, which is resistive to chemicals having a high pH like, for example, DPP and PCI. The compartments are formed by heat sealing two sheets of Cryovac M312 together. Holes 396 are used to hang the bag.

Port 366 (see FIG. 12) sits on port 302, and is for receiving an additional connector associated with a bag that holds the enzyme for processing biological cells. The enzyme bag connector snaps into slots 397 of port 366 and seals with an O-ring in port 302 in a manner similar to cylindrical extensions 375–378.

Having thus described certain embodiments of the present invention, various alterations, modifications, and improvements will readily occur to those skilled in the art. Such alterations, modifications, and improvements are intended to be within the spirit and scope of the invention. Accordingly, the foregoing description is by way of example only, and not intended to be limiting. The invention is limited only as defined in the following claims and the equivalents thereof.

What is claimed is:

1. A device for distributing a plurality of fluids in a blood processing apparatus comprising:
   a plurality of ports for receiving a plurality of different fluids;
   a channel coupled to said plurality of ports;
   a first port coupled to said channel adapted to transfer fluid from said plurality of ports to a first destination, and to receive fluid from said first destination; and
   a second port coupled directly to said channel adapted to transfer fluid received on said first port from said first destination directly to a second destination;
   wherein said channel is coupled to said plurality of ports via a pump.

2. A device for distributing a plurality of fluids comprising:
   a plurality of ports for receiving a plurality of fluids;
   a channel coupled to said plurality of ports;
   a first port coupled to said channel adapted to transfer fluid from said plurality of ports to a processing module and to receive fluid from said processing module; and
   a second port coupled to said channel adapted to transfer fluid received on said first port from said processing module to a destination;
   wherein the processing module is adapted to assure processing conditions by control of pressure, temperature, and processing time of the fluids.

3. A device for distributing a plurality of fluids comprising:
   a plurality of ports for receiving a plurality of fluids;
   a channel coupled to said plurality of ports;
   a first port coupled to said channel adapted to transfer fluid from said plurality of ports to a processing module and to receive fluid from said processing module; and
   a second port coupled to said channel adapted to transfer fluid received on said first port from said processing module to a destination;
   wherein the processing module is adapted to assure processing conditions by varying the volume of the processing module.

4. A device for distributing a plurality of fluids comprising:
   a plurality of ports for receiving a plurality of fluids;
   a channel coupled to said plurality of ports;
   a first port coupled to said channel adapted to transfer fluid from said plurality of ports to a processing module and to receive fluid from said processing module; and
   a second port coupled to said channel adapted to transfer fluid received on said first port from said processing module to a destination;
   wherein the processing module is adapted to transfer fluid out of said processing module by varying the volume of the processing module.

5. A device for distributing a plurality of fluids comprising:
   a plurality of ports for receiving a plurality of fluids;
   a channel coupled to said plurality of ports;
   a first port coupled to said channel adapted to transfer fluid from said plurality of ports to a processing module, and to receive fluid from said processing module;
   a second port coupled to said channel adapted to transfer fluid received on said first port from said processing module to a destination; and
   a control module including an algorithm, the algorithm having variable inputs which control one or more of the temperature, pressure, volume and processing time of the processing module.

6. A device for distributing a plurality of fluids comprising:
   a plurality of ports for receiving a plurality of fluids;
   a channel coupled to said plurality of ports;
   a first port coupled to said channel adapted to transfer fluid from said plurality of ports to a processing module, and to receive fluid from said processing module;
   a pump for controlling the transfer of fluids to the processing module; and
   a control module including an algorithm, the algorithm having variable inputs which control the pump and one or more of the temperature, pressure, volume and processing time of fluids transferred to the processing module.

7. A device for distributing a plurality of fluids comprising:
   a plurality of ports for receiving a plurality of fluids;
   a channel having two or more valves coupled to said plurality of ports;
   a first port coupled to said channel adapted to transfer fluid from said plurality of ports to a processing module, and to receive fluid from said processing module;
   a pump for controlling the transfer of fluids to the processing module; and
   a control module including an algorithm, the algorithm having variable inputs which control opening and closing of the valves and one or more of the temperature, pressure, volume and processing time of fluids transferred to the processing module.

* * * * *